United States Patent [19]

Irie et al.

[11] Patent Number: 5,226,317
[45] Date of Patent: Jul. 13, 1993

[54] METHOD FOR MEASURING CONCENTRATION OF NONVOLATILE CONTENTS OF ELECTRODEPOSITION PAINT

[75] Inventors: Tomoyuki Irie, Osaka; Ikuo Tochizawa, Kawanishi; Hitoshi Kawai, Neyagawa, all of Japan

[73] Assignee: Nippon Paint Co., Ltd., Osaka, Japan

[21] Appl. No.: 687,652

[22] Filed: Apr. 19, 1991

[30] Foreign Application Priority Data

Apr. 21, 1990 [JP] Japan ................... 2-105897

[51] Int. Cl.$^5$ .................. G01N 29/16; G01N 29/02
[52] U.S. Cl. ................... 73/61.79; 73/64.53; 204/299 EC
[58] Field of Search ............. 73/61.79, 61.45, 61.49, 73/64.53; 204/299 EC, 300 EC

[56] References Cited

U.S. PATENT DOCUMENTS

| | | | |
|---|---|---|---|
| 3,359,788 | 12/1967 | Colvin | 73/61.49 |
| 3,475,316 | 10/1969 | DeVittorio | 204/299 EC |
| 4,907,453 | 3/1990 | Marlow et al. | 73/61.79 |
| 4,983,270 | 1/1991 | Kikuta et al. | 204/299 EC |

Primary Examiner—Hezron E. Williams
Assistant Examiner—Rose M. Finley
Attorney, Agent, or Firm—Armstrong, Westerman, Hattori, McLeland & Naughton

[57] ABSTRACT

To obtain an accurate concentration of nonvolatile contents promptly and easily, an electrodeposition paint of which pH, temperature, and organic solvent concentration are in specified ranges is irradiated with ultrasonic waves, and its damping factor is measured, and on a basis of the result from the measurement, the concentration of nonvolatile contents in the electrodeposition paint is determined.

2 Claims, 3 Drawing Sheets

Fig.3
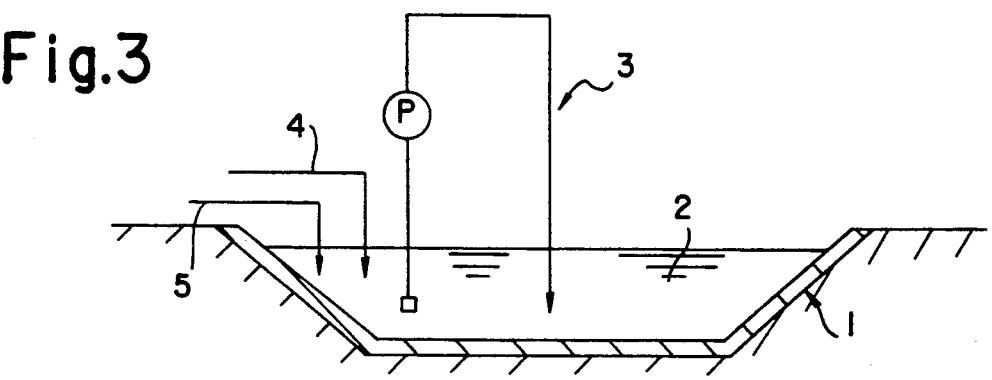
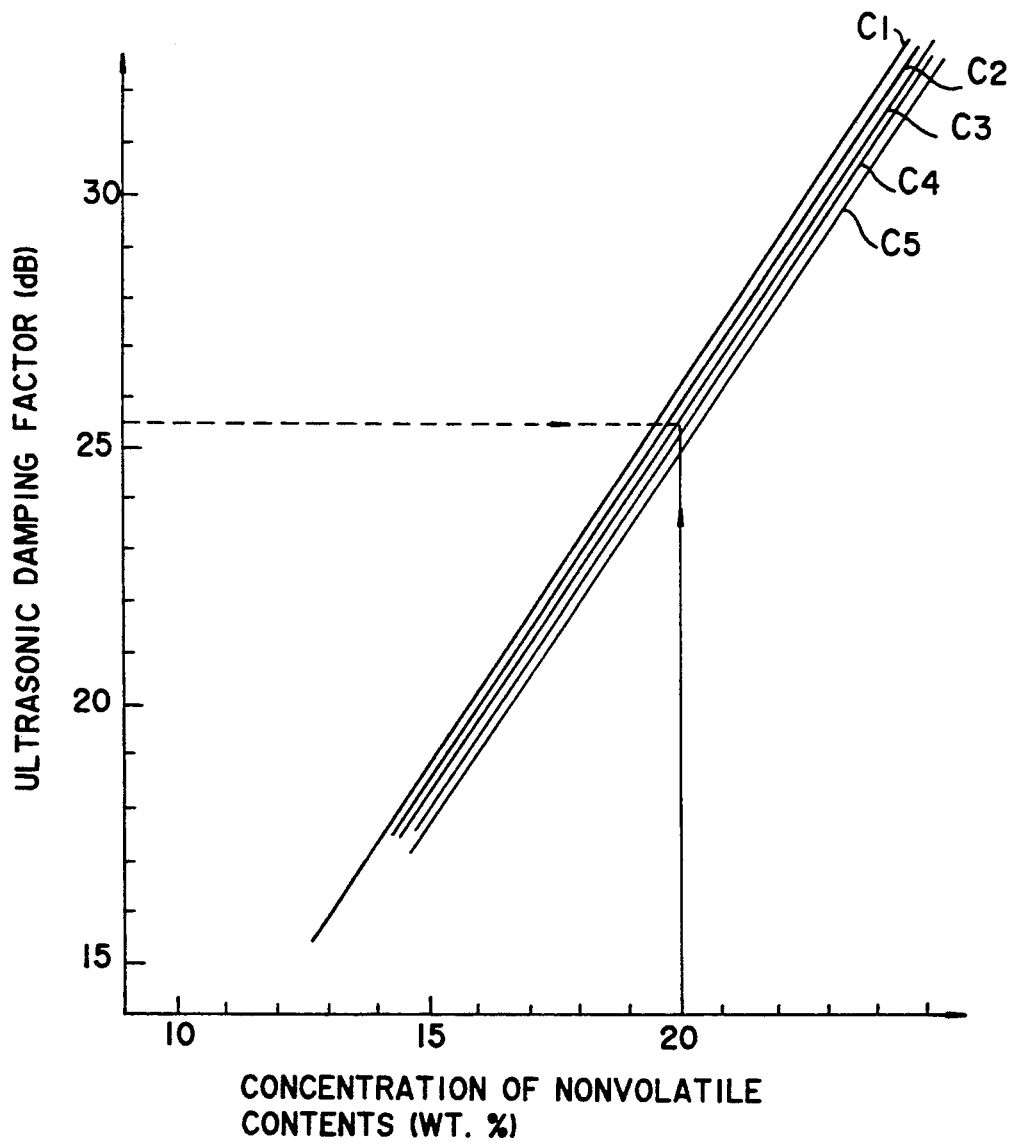
Fig.4

METHOD FOR MEASURING CONCENTRATION OF NONVOLATILE CONTENTS OF ELECTRODEPOSITION PAINT

BACKGROUND OF THE INVENTION

The present invention relates to a method for measuring a concentration of nonvolatile contents of an electrodeposition paint.

Automobiles and building articles are generally coated by electrodeposition coating. The electrodeposition coating line comprises, aside from an electrodeposition bath for immersing an article to be coated (hereinafter, referred simply to as "coating article"), a paint circulating means and other attached facilities, and the electrodeposition bath is, as a matter of fact, filled with an electrodeposition paint. An electrodeposition paint contains nonvolatile components such as a pigment and water-based resin (a water-soluble or water-dispersible resin) in a solution composed of a considerable amount of water and a certain amount of an organic solvent, and when the coating article is immersed in the electrodeposition bath and an electric voltage is applied, the pigment and resin are deposited (electrodeposit) on the coating article by electrophoresis and the coating is achieved. The organic solvent is used, meanwhile, for improving gloss or smoothness of the coating film.

As the coating progresses, the pigment and resin in the bath are consumed, and the concentration of nonvolatile contents lowers, and it is hence necessary to supplement the consumed portion. In order to compensate for the consumption, it is required to know the concentration of nonvolatile contents in the electrodeposition bath. Hitherto, because no method was known for easily measuring the concentration of nonvolatile contents, there has been employed a bath control method which comprises supplementing the paint in proportion to the approximate coating area of the coating article, or supplementing a specific volume of paint at specific time intervals; thereby, compensating for the consumption of the pigment and resin. Such a bath control method is likely to cause fluctuations in the concentration of nonvolatile contents in the electrodeposition bath.

Moreover, deposited amounts of pigment and resin in coating are not always proportional to a pigment concentration and resin concentration in the bath, and if not proportional, as the coating progresses, the ratio of pigment to resin continues to change. Further, mass sediment may be formed due to insufficient agitation in the bath or impurities brought into the bath from outside which may consequently cause variation of the ratio of pigment to resin. In this way, the concentration ratio of pigment to resin in the bath is often deviated largely from an initial ratio in the bath in the course of coating. In such a case, it is required to know the ratio of the pigment to resin in the concentration of nonvolatile contents, when returning to the initial ratio in the bath by supplementing the pigment and resin.

In an electrodeposition paint, since the pigment and resin are present as nonvolatile contents in the bath control as mentioned above, the nonvolatile contents were, conventionally, measured occasionally by manual work apart from a production line.

The concentration of the total nonvolatile contents totaling the resin and pigment components was measured in the following method of evaporating to dryness.

A specific amount of an electrodeposition paint is placed in a weighing dish, and is dried with heating for 1 to 3 hours, and the weight is measured before and after heating, and an amount of the nonvolatile contents is measured on the basis of this weight difference.

The ratio of the pigment component to resin component in the concentration of nonvolatile contents was also determined by measuring an ash amount according to the following procedure.

A specific amount of an electrodeposition paint is placed in a weighing crucible which has been dried for about 3 hours, and is heated for burning for about 60 minutes at 600°-700° C., and the weight is measured before and after the burning to determine the ash amount on a basis of a weight difference. The ash amount is an amount of the pigment, and a balance of subtracting the ash amount from the above amount of the nonvolatile contents is the resin content so that the ratio of the pigment to resin in the concentration of nonvolatile contents is known.

The conventional method, however, had the following problems.

First, it took a relatively long time in measuring the concentration of nonvolatile contents, although the measuring operation is easy. However, there are often a case of an electrodeposition paint where a component ratio in the concentration of nonvolatile contents (for example, the ratio of pigment content to resin content) does not vary so much, and a case where it is not required to know the ratio of components, but it is enough to know only a total concentration of the components. In these cases, a method of promptly and easily measuring the concentration of nonvolatile contents is keenly desired.

Second, in a case of measuring a ratio of pigment content to resin content in a concentration of nonvolatile contents, measurement of the ash amount is carried out together, but this measurement itself is difficult. For measuring the ash amount, a high temperature heat treating device must be used and careful handling for not scattering the ash is required so that the procedure, becomes difficult which requires an experienced skill. Hence, there is a strong demand for easily measuring the ratio of pigment content to resin content in the concentration of nonvolatile contents.

SUMMARY OF THE INVENTION

In light of the above background, it is hence a first object of the invention to provide a method of promptly and easily measuring the accurate concentration of nonvolatile contents, and a second object thereof is to provide a method of easily measuring a ratio of a pigment content to resin content in the concentration of nonvolatile contents without having to measure an ash amount.

In order to achieve the above objects, the present inventors directed their attention to the method of measuring the concentration of nonvolatile contents by means of ultrasonic waves and studied it from various angles.

As methods of measuring nonvolatile contents in a liquid material by using ultrasonic waves, the sonic speed method and damping factor method are known, but the precision is not enough in the sonic speed method, and the damping factor method involves large measuring errors in cases of electrodeposition paints containing a water-based resin and containing both resin and pigment components, although it is applied in measuring a cement sludge concentration, and therefore, in the both cases the methods was considered hardly practicable.

The inventors investigated in detail an origin of the large measuring errors, and discovered the following three factors as the origin of producing measuring errors.

The first factor is the pH of the electrodeposition paint. Change in pH of an electrodeposition paint leads to changes of a resin-dissolving amount and pigment dispersion resulting in variation of a volumetric concentration; thereby, fluctuating the value measured by the ultrasonic damping factor method.

The second factor is temperature of the electrodeposition paint. Temperature change of an electrodeposition paint also causes a large variation in the volumetric concentration leading to fluctuations of the value measured by the ultrasonic damping factor method. That is, when the temperature varies, resin density changes so that the volumetric concentration fluctuates.

The third factor is concentration of an organic solvent used for the electrodeposition paint. Change of concentration of the organic solvent also cause large variation in the volumetric concentration and also varies the measured value of the ultrasonic damping factor. As concentration of the organic solvent becomes lower, expansion of the resin component becomes smaller, the volumetric concentration becomes lower, and on the other hand, elevation of the concentration of an organic solvent causes the expansion of the resin component larger and raise the volumetric concentration. In any case, the ultrasonic damping factor will consequently increase.

The inventors found that if the pH, temperature, and organic solvent concentration of the electrodeposition paint are controlled within specified ranges when measuring by irradiating ultrasonic waves, the measured value of the ultrasonic damping factor accurately corresponds with the concentration of nonvolatile contents without fluctuating, at high reproducibility, and thus, completed the first invention.

Further continuing the studies, a quantitative relationship between the concentration of nonvolatile contents and the ultrasonic damping factor of electrodeposition paint was investigated in plural or numerous electrodeposition paints differing in a ratio of the pigment to resin contained as nonvolatile components, and thereby, a calibration curve was drawn. Then, the ultrasonic damping factor and concentration of nonvolatile contents (measurable, for example, by the method of evaporating to dryness) of the electrodeposition paints to be studied were measured and the calibration curve showing both the factor and concentration was investigated. It was thus found that a ratio of the pigment to resin in the electrodeposition paint which was used for preparing the calibration curve corresponds to the ratio in the electrodeposition paint to be studied. After this, in successive studies, if the ultrasonic damping factor when measuring the quantitative relationship, and the ultrasonic damping factor of the electrodeposition paint to be studied, are measured in a certain state within a specified range in the same manner as described above, the ultrasonic damping factor in the aforementioned quantitative relationship preliminarily obtained and the ultrasonic damping factor of an electrodeposition paint to be studied satisfactorily led to each other's coincidence lying the concentration of nonvolatile contents between both the factors, and thereby, an accurate ratio of the pigment content to the resin content in an electrodeposition paint to be studied was obtained. These findings led to completion of the second invention.

Accordingly, in the method of measuring the concentration of nonvolatile contents of an electrodeposition paint as set forth in claim 1 for solving the first problem, ultrasonic waves are irradiated to the electrodeposition paint under a condition that the pH, temperature, and organic solvent concentration are in specified ranges. The damping factor is subsequently measured, and the concentration of nonvolatile content of the electrodeposition paint is determined on the basis of the results from this measurement.

In the invention as set forth in claim 2 for solving the second problem, when determining a ratio of the pigment content to the resin content by irradiating ultrasonic waves to an electrodeposition paint containing a pigment and resin as nonvolatile contents and then, by using its damping phenomenon, the ultrasonic irradiation is effected under a condition that the pH, temperature and organic solvent concentration of the electrodeposition paint are in specified ranges, and the quantitative relations of the concentration of nonvolatile contents and ultrasonic damping factor are beforehand determined by plural or numerous electrodeposition paints differing in the ratio of the pigment to resin, and the measurement results of the ultrasonic damping factor and concentration of nonvolatile contents of the electrodeposition paints to be studied are compared with the aforementioned quantitative relations, and thereby, a ratio of the pigment content and resin content in the electrodeposition paint to be studied is determined.

Examples of the electrodeposition paint in the present invention may include an electrodeposition paint containing a water-based resin, and an electrodeposition paint containing both a water-based resin and a pigment. The water-based resin and pigment contained in one electrodeposition paint may not be limited to one type, but plural or numerous types may also be contained.

The water-based resins include, for example, an epoxy-based cationic resin, acrylic resin, and a polybutadiene-denatured epoxy resin.

The pigments include a coloring pigment such as carbon black and titanium oxide, and a body pigment such as aluminum silicate.

Of the solvents, organic solvents may include, among others a cellosolve-based solvent, practically butyl cellosolve and ethyl cellosolve, etc.

Practical figures in specified ranges of temperature, pH, organic solvent concentration in a solvent may be determined depending on a type of the electrodeposition paint and precision in controlling, but judging from the using conditions of ordinary electrodeposition paints, the following ranges are appropriate. That is, the specified temperature ranges is 15° to 35° C.; the specified pH range is 5 to 9; and the specified concentration of an organic solvent is 1 to 5%.

The measurement of a concentration of nonvolatile contents according to the invention as set forth in claim 1 is usually carried out according to the following procedure.

An electrodeposition paint containing a water-based resin or an electrodeposition paint containing a pigment and a water-based resin is prepared at a desired concentration and, while it is diluted stepwise by adding only a deionized water (in the electrodeposition paint containing a pigment and water-based resin, the ratio of a pigment content and a resin content in the concentration of nonvolatile contents not being varied), the ultrasonic damping factor is measured under a condition in a specified range at each concentration (obtained by calculation), and thereby, a quantitative relation between the concentration of nonvolatile contents and ultrasonic damping factor is obtained. The quantitative relation is, as seen in FIG. 1, expressed as a linear calibration curve $A_1$ in which the concentration of nonvolatile contents and the ultrasonic damping factor (a dB display) are in linear proportion.

When it is desired to know the concentration of nonvolatile contents in an electrodeposition paint on the electrodeposition coating line using an electrodeposition paint of which calibration curve $A_1$ has been already prepared, measurement of the ultrasonic damping factor of the electrodeposition paint is carried out under a condition in a specified range. When the measured damping factor $S_1$ is applied to the calibration curve $A_1$, the concentration of nonvolatile contents $D_1$ is immediately known.

The ultrasonic damping factor $S_1$ is promptly and easily measured. The measured ultrasonic damping factor $S_1$ is always accurately corresponding to the concentration of nonvolatile contents, and the reliability of measured concentration $D_1$ is high.

Next, the measurement of a ratio of the pigment content to resin content in the concentration of nonvolatile contents according to the invention as set forth in claim 2 is described below.

An electrodeposition paint containing a pigment and water-based is prepared in a desired concentration and, while it is diluted stepwise by adding only deionized water (in an electrodeposition paint containing a pigment and water-based resin, the ratio of the pigment to resin in the concentration of nonvolatile not being varied), the ultrasonic damping factor is measured at each concentration (obtained by calculation) in the specified range, and a quantitative relation between the concentration of nonvolatile contents and the ultrasonic damping factor is obtained. When expressed as a calibration curve, as shown in FIG. 2, a straight calibration curve $a_1$ is obtained, wherein the concentration of nonvolatile contents and ultrasonic damping factor (a dB display) are in linear proportion.

Then, by varying a ratio of the pigment content and the resin content and with a procedure similar to the above, the calibration curve $a_2$ and calibration curve $a_3$ are obtained one after one.

When it is desired to measure concentrations of the pigment contents and resin contents in the concentration of nonvolatile contents in the electrodeposition paints on the electrodeposition coating line using electrodeposition paints for which the calibration curves $a_1$ ... have been already prepared, a specific amount of the electrodeposition paint is sampled and, while the concentration of nonvolatile contents $D_2$ is measured by the method of evaporating to dryness, the ultrasonic damping factor $S_2$ is measured under a condition in a specified range. Applying the results obtained to FIG. 2, a calibration curve on which both the concentration of nonvolatile contents $D_2$ and the ultrasonic damping factor $S_2$ fit simultaneously is searched. The ratio of the pigment to resin in the electrodeposition paint used in preparation of the corresponding calibration curve $a_2$ is a desired value.

Measurement of the ash content is unnecessary at all. Measurements of concentration of nonvolatile contents by the method of evaporating to dryness as well as ultrasonic damping factor show no difficulty. Of course, the ultrasonic damping factor always accurately corresponds to the concentration of nonvolatile contents, and reliability of the measurement results is high.

As described herein, in measurement of the concentration of nonvolatile contents of an electrodeposition paint according to the invention as set forth in claims 1 and 2, since the ultrasonic damping factor of the electrodeposition paint is always measured under a condition in specified ranges of the pH, temperature and organic solvent concentration, the obtained measurement results of the concentration of nonvolatile contents and a ratio of pigment to resin are very high in reliability.

Besides, in the measurement method as claimed in claim 1, as a matter of fact, only the ultrasonic damping factor is measured and the measurement results are promptly obtained; and also, since measurement of the ash content is unnecessary in the measurement method as claimed in claim 2, the measurement results are easily obtained.

BRIEF DESCRIPTION OF THE DRAWING

FIG. 3 is an explanatory diagram showing an approximate structure of an electrodeposition coating device used in the embodiment of this invention, FIG. 4 is a graph showing a calibration curve expressing a quantitative relationship between the concentration of nonvolatile contents and the ultrasonic damping factor in Example 1.

DESCRIPTION OF THE PREFERRED EMBODIMENTS

Figure 1:
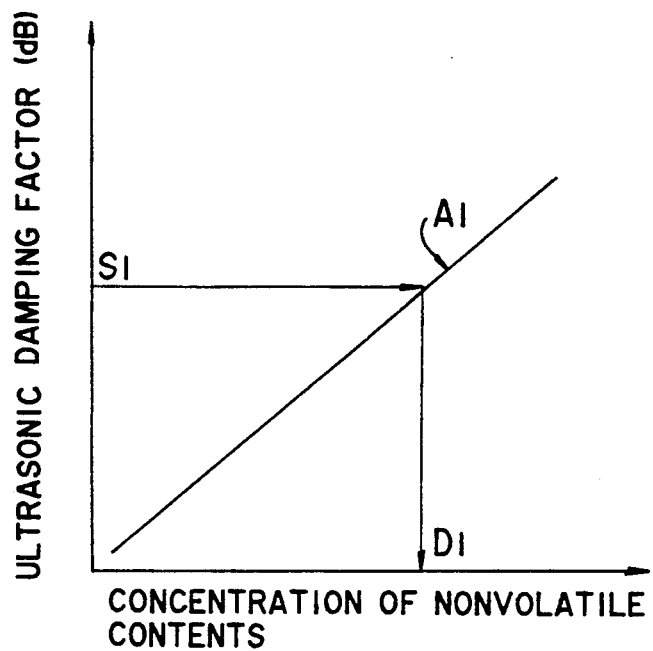
FIG. 1 is a graph showing a calibration curve expressing a quantitative relationship between the concentration of nonvolatile contents and the ultrasonic damping factor in the embodiment of the invention as set forth in claim 1.
Figure 2:
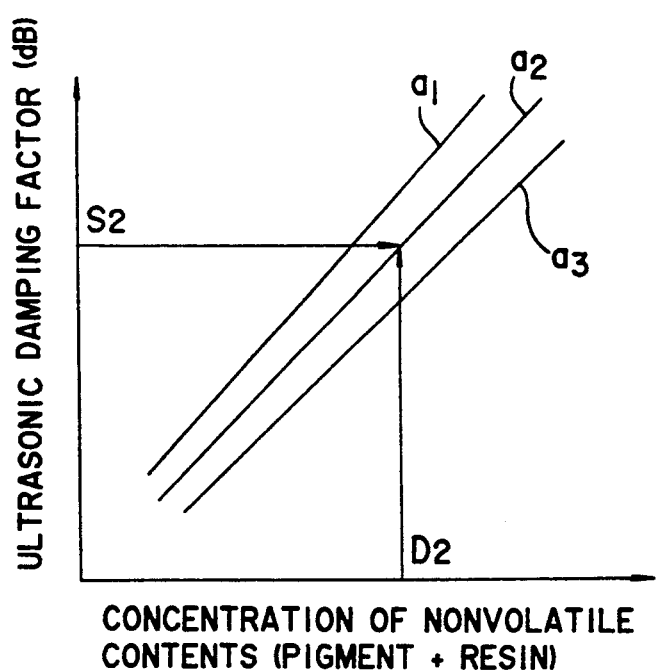
FIG. 2 is a graph showing a calibration curve expressing a quantitative relationship between the concentration of nonvolatile contents and the ultrasonic damping factor in the embodiment of the invention as set forth in claim 2.

Examples are described in detail below.

A method of using one type of a paint for supplementing containing a pigment and resin in a specified concentration is included as a method of supplementing a paint in a line of using an electrodeposition paint containing a pigment and resin, but the following two-liquid supplementing method is often employed. That is, there are arranged a supplementing line for a refill paint F-1 containing a large amount of a pigment in a solvent and a small amount of a water-based resin for dispersing the pigment and a supplementing line for a refill paint F-2 containing only the water-based resin in a solvent; and then, during coating, the concentration of nonvolatile contents in the electrodeposition bath and a ratio of the resin to pigment are occasionally measured, and the refill paint F-1 and F-2 are supplemented from the two supplementing lines so that these measurements may be maintained within allowable ranges based on a standard condition. This is because the two-liquid supplementing method is easier in changing and setting of a mutual ratio of the pigment and resin in the bath as compared with the one-liquid supplementing method.

FIG. 3 shows an embodiment of electrodeposition coating device in which the bath is controlled by the method of measuring the concentration of the nonvolatile contents in the examples.

More specifically, the electrodeposition bath 1 is filled with an electrodeposition paint 2; and the electrodeposition paint 2 is always circulated through a circulation route 3 containing a circulation pump P. The electrodeposition bath 1 is provided with a feed line 4 for the refill paint F-1 and a feed line 5 for the refill paint F-2.

The ultrasonic damping factor is measured under a condition in the aforementioned specified range by sampling a specific amount of the electrodeposition paint from the electrodeposition bath 1. It is of course possible to measure the damping factor in an on-line system by arranging a means for measuring the ultrasonic damping factor to the electrodeposition bath 1. In this case, needless to say, the electrodeposition paint is controlled so as to be under a condition in the specified range at the time of measurement.

The concentration of nonvolatile contents by the method of evaporating to dryness is measured by sampling a specific amount of the electrodeposition paint from the electrodeposition bath 1.

EXAMPLE 1

Electrodeposition paint to be used:
A cationic paint made by Nippon Paint Co., Ltd. tradename PTU-501 Black.
This electrodeposition paint is composed of the following refill paints F-1 and F-2.

| Refill paint F-1 | |
|---|---|
| Resin: (An epoxy based cationic resin) | 10.06 wt. % |
| Pigment: (Carbon black, titanium oxide, etc.) | 31.45 wt. % |
| Solvent: | |
| Deionized water | 52.48 wt. % |
| Organic solvent (ethyl cellosolve, butyl cellosolve) | 6.01 wt. % |
| Total | 100 wt. % |
| Refill paint F-2 | |
| Resin: (An epoxy based cationic resin) | 36.0 wt. % |
| Solvent: | |
| Deionized water | 61.75 wt. % |
| Organic solvent (ethyl cellosolve, butyl cellosolve) | 2.25 wt. % |
| Total | 100 wt. % |

The ultrasonic damping factor was measured by using an oscillator model UAM-2 of an immersing type (made by Tyo-onpa Kogyo Co., Ltd.). The measuring frequency was 3 MHz.

First, the refill paints F-1 and F-2 were mixed in the following ratio (by weight) to prepare an electrodeposition paint, and the concentration was diluted stepwise, and the ultrasonic damping factor was determined at each concentration to obtain a calibration relationship, and the calibration curves C1–C5 were prepared as shown in FIG. 4.

| | F-1:F-2 | Calibration curve |
|---|---|---|
| Electrodeposition paint a | 1:0.5 | $C_1$ |
| Electrodeposition paint b | 1:1 | $C_2$ |
| Electrodeposition paint c | 1:1.94 | $C_3$ |
| Electrodeposition paint d | 1:3.07 | $C_4$ |
| Electrodeposition paint e | 1:4.29 | $C_5$ |

On the other hand, in the coating line using the electrodeposition paint which has a standard ratio of F-1:F-2=1:3.07 or Pigment:Resin=1:3.83. A ratio of Pigment and Resin in nonvolatile contents was measured about the electrodeposition paint which might have said standard ratio.

The fact was that an ultrasonic damping factor was measured by irradiating ultrasonic waves and that a concentration of nonvolatile contents was measured by the method of evaporating to dryness. The measurement results were 25.5 dB and 20.0% for the ultrasonic damping factor and concentration of nonvolatile contents, respectively. The measurement results were then referred to the calibration curves C1–C5, as illustrated in FIG. 4.

Referring to FIG. 4, both the measured values are on the calibration curve C3, and it is understood that the values are ratios of the pigment and resin in the case of F-1:F-2=1:1.94 (pigment:Resin=1:2.54)

In this painting line, since the standard ratio is 1:3.07, it is known that the refill paint F-1 is under an execessive condition (that is, the resin consumption being large). Therefore, when supplementing, the refill paint F-2 should be added slightly more than the standard.

Meanwhile, the specified ranges in measuring the ultrasonic damping factor were as follows.

| (1) | Temperature range | Approximately 28° C.; |
|---|---|---|
| (2) | pH | 6.0–6.3; and |
| (3) | Organic solvent concentration | 2–5 wt. % |

Besides, the result combined with the conventional ash content measurement showed as F-1:F-2=1:1.93 which suggests that a precise result would be obtained without measuring the ash content in the present invention.

EXAMPLE 2

Electrodeposition paint to be used:
A cationic paint made by Nippon Paint Co., Ltd. tradename PTU-80 Gray.
This electrodeposition paint is composed of the following refill paints F-1 and F-2.

| Refill paint F-1 | |
|---|---|
| Resin: (An epoxy-based cationic resin) | 9.68 wt. % |
| Pigment: (Carbon black, titanium oxide, etc.) | 46.35 wt. % |
| Solvent: | |
| Deionized water | 39.45 wt. % |
| Organic solvent (ethyl cellosolve, butyl cellosolve) | 4.52 wt. % |
| Total | 100 wt. % |
| Refill paint F-2 | |
| Resin: (An epoxy-based cationic resin) | 36.0 wt. % |
| Solvent: | |
| Deionized water | 59.17 wt. % |
| Organic solvent (ethyl cellosolve, butyl cellosolve) | 4.83 wt. % |

| | | |
|---|---|---|
| | -continued | |
| Total | | 100 wt. % |

The ultrasonic damping factor was measured by an oscillator model UAM-2 of an immersing type (Tyoonpa Kogyo Co., Ltd.). The measuring frequency was 3 MHz.

Figure 5:
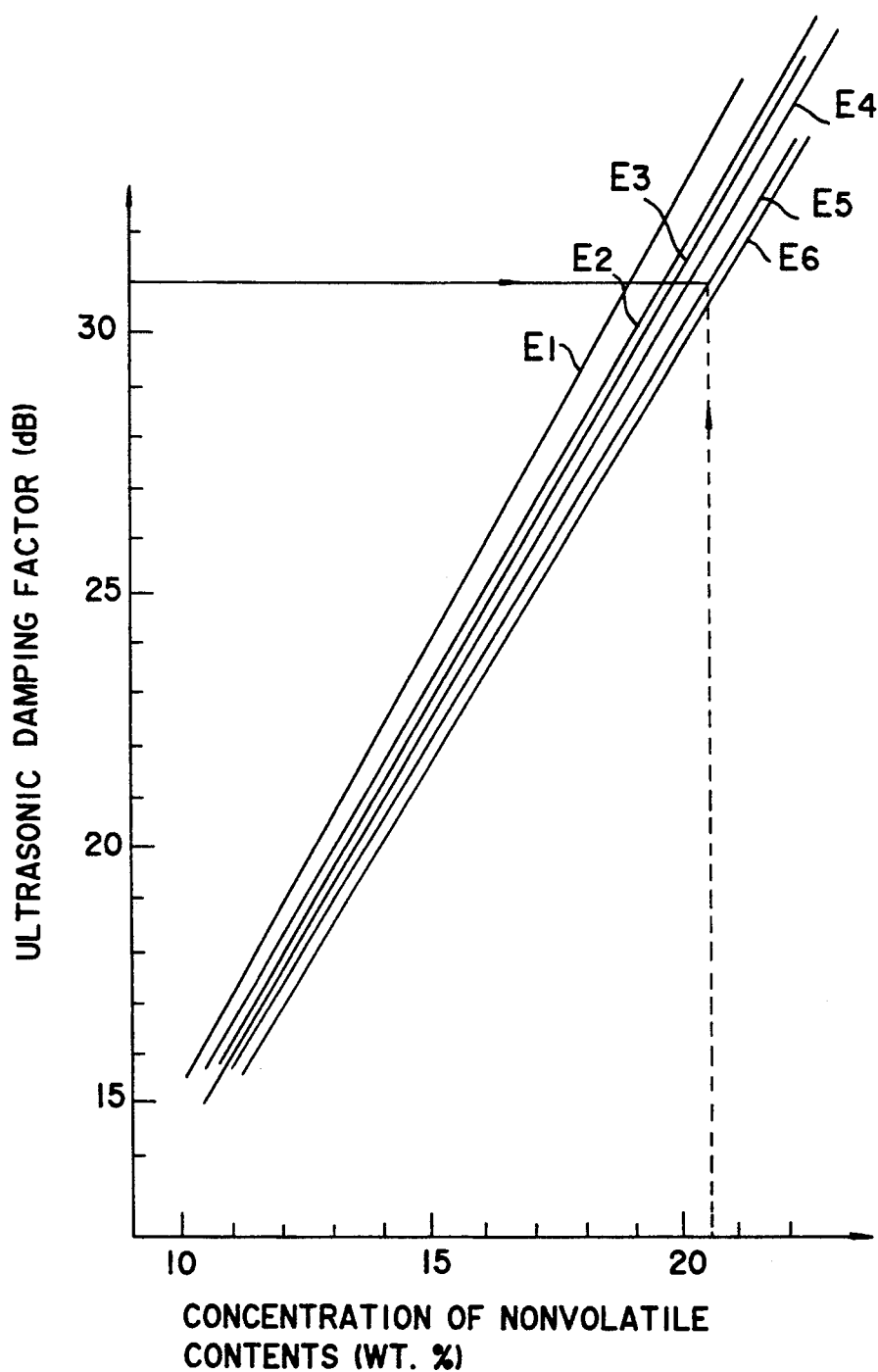
FIG. 5 is a graph showing a calibration curve expressing a quantitative relationship between the concentration of nonvolatile contents and the ultrasonic damping factor in Example 2.

The refill paints F-1 and F-2 were mixed in the following ratio to prepare an electrodeposition paint, and the concentration was diluted stepwise, and the ultrasonic damping factor was measured at every concentration to obtain a calibration relationship, and calibration curves E1-E6 were prepared as shown in FIG. 5.

| | F-1:F-2 | Calibration curve |
|---|---|---|
| Electrodeposition paint a' | 1:1.07 | $E_1$ |
| Electrodeposition paint b' | 1:1.57 | $E_2$ |
| Electrodeposition paint c' | 1:1.73 | $E_3$ |
| Electrodeposition paint d' | 1:2.33 | $E_4$ |
| Electrodeposition paint e' | 1:2.90 | $E_5$ |
| Electrodeposition paint f' | 1:3.90 | $E_6$ |

On the other hand, in the coating line using the electrodeposition paint which has a standard ratio of F-1:F-2=1:2.33 or Pigment:Resin=1:2.02. A ratio of Pigment and Resin in nonvolatile contents was measured about the electrodeposition paint which might have said standard radio.

The fact was that an ultrasonic damping factor was measured by irradiating ultrasonic waves and that a concentration of nonvolatile contents was measured by the method of evaporating to dryness. The measurement results were 31.0 dB and 20.4% for the ultrasonic damping factor and concentration of nonvolatile contents, respectively. The measurement results were then referred to the calibration curves E1-E6, as shown in FIG. 5.

Referring to FIG. 5, both the measured values are on the calibration curve $E_5$, and it is found that the values are ratios of the pigment and resin in the case of F-1:F-2=1:2.90 (pigment:Resin=1:2.46).

Since this coating line is a case where the standard is F-1:F-2=1:2.33, it is known that the refill paint F-2 is under an excessive condition (that is, the pigment consumption is more). Therefore, when supplementing, the refill paint F-1 is added slightly more than the standard.

Specified ranges in measuring the ultrasonic damping factor were as follows.

| (1) | Temperature range | Approximately 28° C.; |
|---|---|---|
| (2) | pH | 5.9–6.3; and |
| (3) | Organic solvent concentration | 2–4.5 wt. %. |

Besides, the result combined with the conventional ash content measurement showed as F-1:F-2=1:2.90, and it is confirmed that a precise result is obtained in this invention without measuring the ash content.

Moreover, for example, in Example 2, if a ratio of the pigment to the resin does hardly change, the concentration of nonvolatile contents is immediately known from the calibration curve $E_4$ by measuring the ultrasonic damping factor of the electrodeposition paint in the bath 1.

The present invention is not limited to the resin and pigment as shown above and as shown in the examples. For example, the method as claimed in Claim 1 may be applied for a control process, which comprises storing the quantitative relation obtained beforehand in a computer, measuring and reading the ultrasonic damping factor in an on-line system, determining the concentration of nonvolatile contents by the calibration program, and feeding back to a coating line. Also, the method as claimed in Claim 2 may be applied for a control process, which comprises storing the quantitative relation obtained beforehand in a computer, measuring the ultrasonic damping factor and the concentration of nonvolatile contents, and inputting the measured results in the computer, determining the ratio of pigment to resin by the calibration program, and feeding back to a coating line.

What is claimed is:

1. A method for measuring a concentration of nonvolatile contents in an electrodeposition paint, wherein irradiation of ultrasonic waves is carried out under the condition that each of a pH, temperature, and an organic solvent concentration of an electrodeposition paint is defined in a specified range, said method comprising:
   determining beforehand a relationship between a concentration of nonvolatile contents and an ultrasonic damping factor in each of a plurality of electrodeposition paints which differ in a concentration of nonvolatile contents and which have the same ratio of the pigment content to the resin content;
   irradiating ultrasonic waves onto a testing electrodeposition paint;
   measuring an ultrasonic damping factor of said testing electrodeposition paint;
   referring said measured damping factor to said relationship between said concentration of nonvolatile contents and said ultrasonic damping factor; and
   determining a concentration of the nonvolatile contents in the testing electrodeposition paint on a basis of the referred result of said measured damping factor.

2. A method for measuring a concentration of nonvolatile contents in an electrodeposition paint, when irradiating ultrasonic waves onto a testing electrodeposition paint containing pigment and resin components as nonvolatile contents, utilizing a damping phenomenon, and determining a ratio of pigment content to resin content, wherein irradiation of ultrasonic waves is carried out under the condition that each of a pH, temperature, and an organic solvent concentration of an electrodeposition paint is defined in a specified range, said method comprising:
   determining beforehand a relationship between a concentration of nonvolatile contents and an ultrasonic damping factor in each of a plurality of electrodeposition paints which differ in a concentration of nonvolatile contents and which have the same ratio of the pigment content to the resin content, and further determining at least one relationship about electrodeposition paints which have a different ratio of the pigment content to the resin content;
   measuring an ultrasonic damping factor of said testing electrodeposition paint;
   measuring a concentration of nonvolatile contents of said testing electrodeposition paint;
   referring the measurement results of the ultrasonic damping factor and the concentration of nonvolatile contents in said testing electrodeposition paint to the above-determined relationship between said concentration of nonvolatile contents and said ultrasonic damping factor; and thereafter
   determining the ratio of the pigment content to the resin content in the testing electrodeposition paint.

* * * * *